US008975431B2

United States Patent
Mercier et al.

(10) Patent No.: US 8,975,431 B2
(45) Date of Patent: Mar. 10, 2015

(54) PROCESS FOR PREPARING AN ORTHO-SUBSTITUTED 5-HALOPHENOL AND A SYNTHESIS INTERMEDIATE THEREOF

(75) Inventors: Claude Mercier, Shanghai (CN); Floryan De Campo, Shanghai (CN); Sébastien Righini, Lyons (FR)

(73) Assignees: Rhodia Operations, Paris (FR); Solvay (China) Co., Ltd., Shanghai (CN)

( * ) Notice: Subject to any disclaimer, the term of this patent is extended or adjusted under 35 U.S.C. 154(b) by 0 days.

(21) Appl. No.: 13/698,985

(22) PCT Filed: May 19, 2010

(86) PCT No.: PCT/CN2010/072947
§ 371 (c)(1),
(2), (4) Date: Nov. 19, 2012

(87) PCT Pub. No.: WO2011/143819
PCT Pub. Date: Nov. 24, 2011

(65) Prior Publication Data
US 2013/0066097 A1 Mar. 14, 2013

(51) Int. Cl.
C07C 309/75 (2006.01)
C07C 41/01 (2006.01)
C07C 303/28 (2006.01)
C07C 41/26 (2006.01)
C07C 303/30 (2006.01)

(52) U.S. Cl.
CPC ............... *C07C 303/28* (2013.01); *C07C 41/26* (2013.01); *C07C 303/30* (2013.01)
USPC ............................................. 558/56; 568/653

(58) Field of Classification Search
USPC ............................................ 558/56; 568/653
See application file for complete search history.

(56) References Cited

U.S. PATENT DOCUMENTS

| 2003/0092946 A1* | 5/2003 | Mioskowski et al. ......... 568/784 |
| 2003/0216592 A1 | 11/2003 | Kawahara et al. |
| 2004/0024257 A1 | 2/2004 | Vastra et al. |

FOREIGN PATENT DOCUMENTS

| CN | 1391553 A | 1/2003 |
| CN | 1473149 A | 2/2004 |
| CN | 1706786 A | 12/2005 |
| WO | 94/12461 A1 | 6/1994 |

OTHER PUBLICATIONS

English Translation of First Official Action corresponding to Chinese Patent Appln No. 201080067526.1, dated Jun. 28, 2013, pp. 1-8.
First Official Action corresponding to Chinese Patent Appln No. 201080067526.1, dated Jun. 28, 2013, pp. 1-9.
Tang, "Chemistry and Technology of Refined Organic Synthesis", Chemical Industry Press, Jan. 31, 2002, p. 63, Beijing.
Yao et al., "Synthesis Principle of Fine Chemical", China Petrochemical Press Co. LDT., Mar. 31, 2000, pp. 314-316, Beijing.
International Search Report issued on Feb. 10, 2011, by the European Patent Office as the International Searching Authority in International Patent Application No. PCT/CN2010/072947.
Written Opinion of the International Searching Authority issued on Feb. 10, 2011, in International Patent Application No. PCT/CN2010/072947.
Notice of Reason(s) for Refusal dated Jan. 21, 2014 corresponding to Japanese Patent Application 2013-510471, with English translation, 6 pp.
Ajda Podgorsek, Stojan Stavber, Marko Zupan, and Jernej Iskra. "Environmentally benign electrophilic and radical bromination 'on water': H2O2—HBr system versus N-bromosuccinimide" Tetrahedron (2009), 65, pp. 4429-4439.

\* cited by examiner

*Primary Examiner* — Kristin Vajda

(57) ABSTRACT

A process for preparing a 5-halophenol, ortho-substituted by an electron-donating group, is described. Also described, is a process for preparing a sulphonic ester of an ortho-substituted phenol, which is the synthesis intermediate for the ortho-substituted 5-halophenol. The process for preparing a phenol ortho-substituted by an electron-donating group and protected in the form of a sulphonic ester can include reacting a phenol ortho-substituted by an electron-donating group with a sulphonylating agent in the presence of a Lewis acid. The process for preparing a 5-halophenol ortho-substituted by an electron-donating group can include a first step of preparing a phenol ortho-substituted by an electron-donating group and protected in the form of a sulphonic ester, as described above; a second step of halogenating the protected phenol intermediate obtained in the preceding step, in the position para to the electron-donating group; and a third step of deprotecting the sulphonic ester function to hydroxyl.

32 Claims, No Drawings

PROCESS FOR PREPARING AN ORTHO-SUBSTITUTED 5-HALOPHENOL AND A SYNTHESIS INTERMEDIATE THEREOF

CROSS-REFERENCE TO PRIOR APPLICATION(S)

This application is a National Stage of PCT/CN2010/072947, filed May 19, 2010, and designating the United States (published in English on Nov. 24, 2011, as WO 2011/143819 A1; the title and abstract were also published in English).

FIELD OF THE INVENTION

The present invention relates to a process for preparing a 5-halophenol which is ortho-substituted by an electron-donating group.

The invention pertains more particularly to the preparation of 5-bromo-2-methoxyphenol, commonly known as 5-bromoguaiacol.

Another subject of the present invention is the process for preparing a sulphonic ester of an ortho-substituted phenol, which is the synthesis intermediate for the ortho-substituted 5-halophenol.

BACKGROUND OF THE INVENTION

The preparation of brominated derivatives of guaiacol, more particularly 6-bromoguaiacol and 4-bromoguaiacol, is described in the literature.

EP 0338898 discloses preparation of 6-bromoguaiacol by bromination of guaiacol in isopropyl ether, using a solution of N,N-dibromo-tert-butylamine in isopropyl ether. The yield obtained is 75%.

According to Thomas Oberhauser (J. Org. Chem. 1997, 62, 4504-4506), guaiacol can be brominated in position 4 using NBS/HBF in acetonitrile. The yield obtained after 7 hours is 72%.

Hence the preparation of brominated derivatives of guaiacol in ortho or para position proves to be relatively easy.

In contrast, the preparation of the derivative 5-bromoguaiacol is much more difficult because the presence of electron-donating hydroxyl and methoxy groups promotes electrophilic substitutions in positions 6 and 4 and therefore leads more readily to the ortho- and para-bromophenol derivatives.

DESCRIPTION OF THE INVENTION

The objective of the present invention is therefore to provide an access route to 5-halophenols which are substituted in ortho position by an electron-donating group, and more particularly to 5-bromoguaiacol.

Another objective of the invention is to provide a process which can be implemented on the industrial scale and which meets the various environmental constraints, more particularly in terms of industrial waste.

A further objective of the invention is to provide a process which produces the derivative brominated in position 5, with a selectivity and a yield compatible with industrial exploitation.

Now found, and provided by the present invention, is a process for preparing a 5-halophenol ortho-substituted by an electron-donating group from a phenol ortho-substituted by an electron-donating group, characterized in that it comprises the following steps:

a first step of preparing a phenol ortho-substituted by an electron-donating group and protected in the form of a sulphonic ester, by reacting the phenol ortho-substituted by an electron-donating group with a sulphonylating agent in the presence of an effective amount of a Lewis acid, a second step of halogenating the protected phenol intermediate obtained in the preceding step, in the position para to the electron-donating group, a third step of deprotecting the sulphonic ester function to hydroxyl.

In the specification below of the present invention, "phenol" means an aromatic molecule which bears at least one hydroxyl group bonded directly to a carbon of a benzene ring.

The ortho-substituted phenol involved in the process of the invention is a phenol which bears an electron-donating group in a position ortho to the hydroxyl group and possesses a hydrogen atom in a position para to the electron-donating group.

In the present text, an "electron-donating group" means a group as defined by H. C. Brown in the Jerry March work Advanced Organic Chemistry, 4th edition, John Wiley and Sons, 1992, chapter 9, pp. 273-292.

Accordingly, the present invention produces a 5-halophenol ortho-substituted by an electron-donating group via intermediate preparation of a sulphonic ester of the phenol ortho-substituted by an electron-donating group.

Another subject of the present invention is the process for preparing a phenol ortho-substituted by an electron-donating group and protected in the form of a sulphonic ester, as prepared in the first step, characterized in that it comprises reacting a phenol ortho-substituted by an electron-donating group with a sulphonylating agent in the presence of an effective amount of a Lewis acid.

Indeed, the process for preparing the sulphonic ester of the ortho-substituted phenol, a protected form of the phenol, is entirely original since, generally, the sulphonylation reaction of a phenol is performed by reacting it with a sulphonylating agent in the presence of a base, for example pyridine or triethylamine (Jerry March, Advanced Organic Chemistry, 5th edition, John Wiley and Sons, 2001, p. 576).

The major drawback of such a process is that it results in waste which is highly pollutive owing to the presence of large amounts of salt formed because the base is used in stoichiometric amount.

The invention therefore provides another process for preparing this synthesis intermediate.

In accordance with the process of the invention, in a first step, the hydroxyl group of the starting phenol is protected.

The starting compound is a phenol which bears at least one electron-donating group in a position ortho relative to the hydroxyl group, and whose position para to the electron-donating group is free of any substituent.

More particularly, the phenol conforms to the general formula (I):

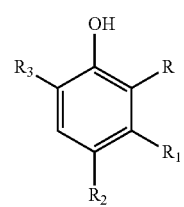

and in said formula (I):
R represents an electron-donating group, and
$R_1$, $R_2$ and $R_3$, which are identical or different, represent:
  a hydrogen atom,
  a linear or branched alkyl group having from 1 to 20 carbon atoms and optionally bearing one or more halogen atoms,
  a cycloalkyl group having from 3 to 8 carbon atoms, and preferably 6 carbon atoms,
  an aralkyl group having from 6 to 20 carbon atoms,
  an aryl group having from 6 to 20 carbon atoms,
  a halogen atom,
  an electron-donating group.

It is possible for this ring to bear a substituent of any other kind, provided that it does not interfere in the desired product.

Accordingly, in the formula (I), the groups $R_1$, $R_2$ and $R_3$ may also represent an electron-withdrawing group.

An "electron-withdrawing group" means a group as defined by H. C. Brown in the Jerry March work Advanced Organic Chemistry, 4th edition, John Wiley and Sons, 1992, chapter 9, pp. 273-292.

It is preferably a carboxyl or ester group (having preferably from 3 to 8 carbon atoms), a nitrile group, a nitro group, a formyl group, an acyl group, for example acetyl.

The compounds employed preferably conform to the formula (I) in which $R_1$, $R_2$ and $R_3$ represent a hydrogen atom, a linear or branched alkyl group having from 1 to 4 carbon atoms, a halogen atom or a trifluoromethyl group.

Of the starting compounds conforming to the formula (I) it is preferred to select those of formula (I) in which R represents one of the following groups or functions:
  a linear or branched alkyl group having preferably from 1 to 6 carbon atoms and more preferably from 1 to 4 carbon atoms,
  a cycloalkyl group having from 3 to 8 carbon atoms, and preferably 6 carbon atoms,
  a phenyl group,
  a benzyl or phenylethyl group,
  a hydroxyl group,
  a fluorine atom,
  an alkoxy group having preferably from 1 to 6 carbon atoms, more preferably from 1 to 4 carbon atoms, in the alkyl moiety, or a phenoxy group,
  a preferably disubstituted amino group in which the identical or different substituents are linear or branched alkyl groups having from 1 to 6 carbon atoms, and preferably from 1 to 4 carbon atoms, or a phenyl group,
  an alkylamide or arylamide group in which the alkyl group has from 1 to 6 carbon atoms, and preferably from 1 to 4 carbon atoms, or a phenyl group.

The compounds employed preferably conform to the formula (I) in which R represents an alkyl group having from 1 to 4 carbon atoms, preferably methyl or ethyl; an alkoxy group having from 1 to 4 carbon atoms, preferably methoxy or ethoxy; or a hydroxyl group.

The compounds employed preferably conform to the formula (I) in which $R_1$, $R_2$ and $R_3$ represent a hydrogen atom.

The process of the invention applies more particularly to the following phenols:
  pyrocatechol,
  o-cresol,
  2-ethylphenol,
  2-propylphenol,
  2-sec-butylphenol,
  2-tert-butylphenol,
  2-methoxyphenol,
  2-ethoxyphenol,
  2,3-dimethylphenol,
  2,6-dimethylphenol,
  vanillin,
  pyrogallol,
  2,3,6-trimethylphenol,
  2,6-di-tert-butylphenol,
  2-phenoxyphenol.

In accordance with the process of the invention, the first step involves protecting the hydroxyl function by converting it to sulphonic ester.

For this purpose the ortho-substituted phenol is reacted with a sulphonylating agent.

This is a compound comprising at least one sulphonyl group of type $—SO_2R_4$ in which $R_4$ represents a hydrocarbon group having from 1 to 20 carbon atoms.

It conforms more particularly to the formula (II) below:

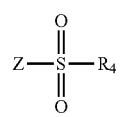

(II)

and in said formula (II):
  $R_4$ represents a hydrocarbon group having from 1 to 20 carbon atoms, and
  Z represents:
    a hydroxyl group or a halogen atom, preferably a chlorine or bromine atom,
    a group $—O—SO_2—R_4'$ in which $R_4'$, which is identical to or different from $R_4$, has the meaning given for $R_4$.

The preferred sulphonylating agents conform to the formula (II) in which Z represents a chlorine or bromine atom.

In the formula (II), $R_4$ represents more particularly:
  an alkyl group having from 1 to 10 carbon atoms, preferably 1 to 4 carbon atoms, and more preferably a methyl or ethyl group, which optionally bears a halogen atom, a $CF_3$ group or an ammonium group $N(R_5)_4$, where $R_5$, identical or different at each occurrence, represents an alkyl group having 1 to 4 carbon atoms,
  a cycloalkyl group having from 3 to 8 carbon atoms, preferably a cyclohexyl group,
  an aryl group having from 6 to 12 carbon atoms, preferably a phenyl group which optionally bears an alkyl group having from 1 to 10 carbon atoms, preferably from 1 to 4 carbon atoms, and more preferably a methyl or ethyl group, a halogen atom, a $CF_3$ group or an $NO_2$ group,
  a group $CX_3$ in which X represents a fluorine, chlorine or bromine atom,
  a $CF_2—CF_3$ group,
  a group $C_p H_a F_b$ in which p represents a number from 1 to 10, b represents a number from 3 to 21, and $a+b=2p+1$.

The preferred sulphonylating agents conform to the formula (II) in which the group $—SO_2—R_4$ represents:
  tosyls (p-toluenesulphonyl)-$SO_2—C_6H_4—CH_3$
  besyls (benzenesulphonyl)-$SO_2—C_6H_5$
  brosyls (p-bromobenzenesulphonyl)-$SO_2—C_6H_4—Br$
  nosyls (p-nitrobenzenesulphonyl)-$SO_2—C_6H_4—NO_2$
  mesyls (methanesulphonyl)-$SO_2—CH_3$
  betyls (ammonioalkanesulphonyl)-$SO_2—(CH_3)_n NMe_3^+$ with n between 0 and 6,
  triflyls (trifluoromethanesulphonyl)-$SO_2—CF_3$
  nonaflyls (nonafluorobutanesulphonyl)-$SO_2—C_4F_9$
  tresyls (2,2,2-trifluoroethanesulphonyl)-$SO_2—CH_2—CF_3$.

Preferred examples of sulphonylating agents employed are more particularly the following compounds:
triflic anhydride,
methanesulphonyl chloride,
trifluoromethanesulphonyl chloride,
benzenesulphonyl chloride,
p-toluenesulphonyl chloride.

In accordance with the process of the invention, the ortho-substituted phenol is reacted with the sulphonylating agent in the presence of an effective amount of a Lewis acid.

The Lewis acids suitable for the implementation of the process of the is invention are compounds comprising a metal or metalloid cation which is said to be "borderline".

Metal or metalloid cations employed are those which are borderline or close thereto.

By "borderline" are meant, according to the invention, not only all of the metal or metalloid cations which are classed as borderline, but also all of those which are classed as hard or soft, with the exception of very hard cations and very soft cations.

A hard cation is defined as an electron acceptor atom, of small or large size and with a strong positive charge, which contains no unpaired electrons in the valency orbital. The cations involved are generally small cations with a high oxidation state which do not possess readily detachable electrons.

Examples of very hard cations include $B^{3+}$, $Mg^{2+}$, $Al^{3+}$, $Si^{4+}$, $Ti^{4+}$, $Mn^{2+}$, $Fe^{3+}$, $Zr^{4+}$ and $La^{3+}$.

A soft cation is defined as an electron acceptor atom, of large or small size and with a weak positive charge, which contains unpaired electrons (p or d) in the valency orbital. The cations involved are generally large cations with a low oxidation state which possess readily detachable electrons.

Examples of very soft cations include $Cu^+$, $Ag^+$ and $Hg^+$.

For the selection of a borderline cation as defined according to the invention, reference may be made to the literature and particularly to the article by Tse-Lok Ho [Chemical Reviews 75; No. 1, pp. 1-20 (1975)].

The borderline cation employed in the process of the invention has an oxidation state of at least +2, preferably of +3, +4 or +5.

Metal or metalloid cations suitable for the invention include in particular those of the metallic or metalloid elements from Groups (IIb), (IVb), (Vb) and (VIb) of the Periodic Table of the Elements.

In the present text, reference hereinafter is to the Periodic Table of the Elements as published in Bulletin de la Société Chimique de France, No. 1 (1966).

Examples of cations very suitable for the process of the invention include more particularly, from those from group (IIb), zinc; from group (IVb), tin; from group (Vb), antimony and bismuth; and, from group (VIb), tellurium.

Among the aforementioned cations it is preferred to select the following: $Zn^{2+}$, $Sn^{2+}$, $Sn^{4+}$, $Sb^{5+}$, $Bi^{3+}$ and $Te^{4+}$, and more preferably $Zn^{2+}$.

With regard to the anions bonded to these cations, mention may be made of hard anions such as $SO_4^{2-}$, $CH_3COO^-$, $C_6H_5COO^-$, $CH_3SO_3^-$ and $CF_3SO_3^-$, or borderline anions such as $Cl^-$, $Br^-$, $NO_2^-$ and $SO_3^{2-}$.

Among the aforementioned anions it is preferred to select $Cl^-$ or $Br^-$.

More specific examples of Lewis acids include the organic salts such as the acetate, propionate, benzoate, methanesulphonate or trifluoromethanesulphonate of the metallic or metalloid elements from the aforementioned groups of the Periodic Table of the Elements.

With regard to the inorganic salts, mention may be made in particular of the chloride, bromide, iodide, sulphate, oxide and analogous products of the metallic or metalloid elements from the aforementioned groups.

It is preferred to select metal halides and more particularly antimony(V), tin(II) or (IV), zinc(II), bismuth(III) and tellurium(IV) chloride or bromide.

Among the aforementioned halides, zinc(II) chloride is preferred.

The invention does not exclude the generation of a halide in situ and hence the use of any compound of the aforementioned elements, provided that it is combined with a halogen source, such as, for example, chlorine, bromine; hydrochloric acid, hydrobromic acid; acetyl chloride; silicon chloride $SiCl_4$; and halosilanes such as $Me_3SiCl$, $Me_2SiCl_2$ and $MeSiCl_3$.

According to the physical form of the Lewis acid employed, catalysis may be homogeneous or heterogeneous.

The Lewis acid is generally employed in a solid form.

It may also be employed in a supported form, by depositing it on an organic or inorganic support. For this purpose, the support may be selected from metal oxides, such as aluminium oxide, silicon oxide, titanium oxide and/or zirconium oxide, clays, and more particularly kaolin, talc or montmorillonite, or else from carbons which are optionally activated by a well-known treatment with nitric acid, or acetylene black or organic polymers, for example the polyvinyl polymers PVC (polyvinyl chloride) or PVDC (polyvinylidene chloride) or polystyrene polymers, which may be functionalized with nitrile functions, or else polyacrylic polymers (and, in particular, direct use of polyacrylonitrile).

The support may be in any form, for example powder, beads, granules, extrudates, etc.

The supported catalyst may be prepared by techniques which are known to a person skilled in the art.

For preparing the supported catalyst useful in implementing the process of the present invention, it is possible to employ conventional techniques, which are known per se, for preparing supported metal catalysts. Reference may be made, in particular, for the preparation of various catalysts, to the J. F. Lepage work "Catalyse de contact" [Contact catalysis], design, preparation and use of industrial catalysts, published by Technip (1978).

The catalyst may be prepared, for example, by introducing a support into a solution which is prepared by dissolving at least one appropriate compound of the selected element or elements; the active element or elements is or are deposited on the support by distilling the solvent, usually water, and the catalyst mass thus obtained is subjected to a drying operation.

In another conventional method of preparation, the compound or compounds providing the active elements is or are deposited on the support by precipitating the compounds in a way which is known per se and by subjecting the catalyst mass thus obtained to drying.

In the description, the term "catalyst" will be used to refer to the catalyst constituted by the Lewis acid or else supported.

The amount of active phase represents from 5% to 100% of the weight of the catalyst. In a supported catalyst, it represents from 5% to 50%, preferably from 5% to 20%, of the weight of the catalyst.

The catalysts may take various forms in the process of the invention: powder, shaped products such as granules (for example extrudates or beads), pellets, which are obtained by extrusion, moulding, compacting or any other type of known process.

According to the process of the invention, the reaction between the ortho-substituted phenol and the sulphonylating agent is conducted in liquid phase, in the presence or in the absence of an organic solvent.

In a first, preferred embodiment of the invention, the reaction is conducted in the absence of organic solvent.

Another variant of the process of the invention comprises conducting the reaction in an organic solvent.

There are a number of imperatives governing the selection of the solvent.

It must be inert under the conditions of the invention, and must have a boiling point higher than the temperature of the reaction.

Preference is given to employing an organic solvent which is aprotic and of low polarity.

Examples of solvents suitable for the present invention include, in particular, halogenated or unhalogenated aliphatic or aromatic hydrocarbons.

Examples of aliphatic hydrocarbons include more particularly paraffins such as, in particular, hexane, heptane, cyclohexane and methylcyclohexane, and aromatic hydrocarbons such as, in particular, toluene, xylenes, cumene, mesitylene, and petroleum fractions composed of a mixture of alkylbenzenes.

The aliphatic or aromatic halogenated hydrocarbons include more particularly dichloromethane, chloroform, tetrachloromethane, 1,2-dichloroethane, trichloroethylene and tetrachloroethylene; and monochlorobenzene, dichlorobenzenes and mixtures thereof.

It is also possible to use a mixture of organic solvents.

As indicated above, the ortho-substituted phenol is reacted with a sulphonylating agent, optionally in a reaction solvent as defined, and in the presence of a Lewis acid catalyst.

The ratio between the number of moles of sulphonylating agent and the number of moles of ortho-substituted phenol may be between 0.9 and 10, and is preferably between 1.0 and 2.0.

The amount of catalyst employed in the process of the invention may vary within wide limits. It may represent—by mass relative to the ortho-substituted phenol employed—from 0.01% to 20%, preferably from 0.05% to 10% and more preferably between 0.1% and 2%.

Where an organic solvent is employed, the amount thereof employed is selected generally such that the concentration of the resulting product is between 10% and 60%, preferably between 20% and 30%.

The temperature at which the sulphonylating reaction is implemented depends on the reactivity of the starting substrate and on that of the sulphonylating agent.

It is situated at between 20° C. and 150° C., preferably at between 70° C. and 120° C.

Generally speaking, the reaction is conducted at atmospheric pressure, although lower or higher pressures may also be suitable. Autogenous pressure is employed when the reaction temperature is higher than the boiling temperature of the reactants and/or products.

According to one preferred variant of the process of the invention, the process of the invention is conducted under a controlled atmosphere of inert gases. A noble gas atmosphere may be established, preferably of argon, although it is more economical to employ nitrogen.

From a practical standpoint, the process may be implemented discontinuously or continuously.

According to a first variant, the sulphonylating agent and the Lewis acid catalyst are introduced.

After the reactants have been contacted, the reaction mixture is brought to the desired temperature with stirring.

Subsequently the ortho-substituted phenol is added, preferably gradually.

Stirring is continued until full consumption of the reactants, which can be monitored by an analytical method, for example by gas chromatography.

At the end of reaction, a liquid phase is recovered which comprises the ortho-substituted and protected phenol.

The subsequent halogenation reaction may be conducted directly in the reaction medium obtained from the first step, or else the ortho-substituted and protected phenol may be recovered in a conventional way, for example by distillation or by crystallization, and preferably by distillation.

After the ortho-substituted and protected phenol has been separated by distillation, a distillation bottom product is obtained which comprises the catalyst, which can be recycled a number of times.

It is also possible to contemplate, at the end of reaction, separating off the catalyst. If the catalyst is insoluble, it can be separated by a solid/liquid separation technique, preferably by filtration.

Where the catalyst is soluble, it is removed by treating the mixture with a complexing agent, for example tartaric acid or sodium carbonate.

In the case of the preparation of 5-bromoguaiacol from guaiacol and mesyl chloride, the hydrochloric acid formed is trapped in a column of base, preferably sodium hydroxide solution.

The reaction mixture obtained comprises 2-methoxy-1-methylsulphonyloxybenzene.

It may be recovered, for example, by distillation, or else the halogenation reaction may be carried out without separation of intermediate.

According to one preferred embodiment of the invention, the halogenation reaction is carried out directly in the reaction mixture obtained, following removal of the excess mesyl chloride by simple distillation.

Accordingly, one advantage of the process of the invention is to be able to recycle the excess, unreacted sulphonylating agent to the start of the process.

The other variant of the invention involves conducting the reaction continuously, in a tubular reactor comprising the solid catalyst arranged in a fixed bed.

The ortho-substituted phenol and the sulphonylating agent may be introduced separately or in a mixture into the reactor.

They may also be introduced into a solvent, as noted above.

The liquid phase obtained is treated as noted above.

The product is an ortho-substituted and protected phenol conforming to the formula (III):

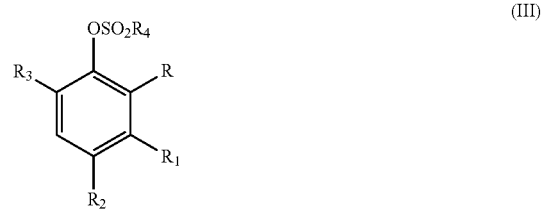

(III)

and in said formula (III), R to $R_4$ have the meaning given above.

In accordance with the process of the invention, a second halogenation step is performed on the phenol conforming to the formula (III).

According to one preferred embodiment of the invention, the halogenation reaction of the benzene ring is performed by reacting the ortho-substituted and protected phenol of the formula (III) with a sufficient amount of a hydrohalic acid HY, with Y representing a halogen atom, preferably chlorine, bromine or iodine, in the presence of an oxidizing agent.

The hydrohalic acid generally employed is hydrochloric acid or, in particular, hydrobromic acid. This hydrohalic acid may be employed as it is in the reaction medium or else may be generated in situ. It will be appreciated that the generation of this hydrohalic acid in situ is one of the skills of a person skilled in the art.

The hydrohalic acid may be employed in the form of a concentrated solution, in the form of an aqueous solution or in gaseous form.

By way of indication, in the specific case of hydrobromic acid, solutions with a concentration of between 40% and 60%, and preferably of the order of 40% to 50%, prove to be preferred.

It is advantageous to use an amount of hydrohalic acid such that the amount of $Y^-$ is at least stoichiometrically equal to that of the starting phenol of formula (III).

However, the presence of a slight excess is preferred.

Hence the ratio of the number of moles of hydrohalic acid to the number of moles of phenol of formula (III) is usually between 1 and 1.5 and preferably between 1.05 and 1.2.

The oxidizing agent is more particularly a compound which possesses a peroxide bond. Advantageously it is a peroxide derivative or peracid derivative, and preferably hydrogen peroxide. Also suitable for the process claimed are oxidizing agents such as $N_2O$.

This oxidizing agent is generally employed in an equimolar amount expressed relative to the hydrohalic acid HY.

The hydrogen peroxide preferably employed in the process of the invention may be in the form of an aqueous solution or an organic solution.

Aqueous solutions, since they are more readily available commercially, are used with preference.

The concentration of the aqueous solution of hydrogen peroxide, although not critical per se, is selected so as to introduce as little water as possible into the reaction mixture. Use is made generally of an aqueous solution of hydrogen peroxide having a concentration of from 20% to 70% by mass, but preferably within the region of 30%.

The amount of hydrogen peroxide employed is generally such that the hydrogen peroxide/phenol of formula (III) molar ratio is usually between 1 and 1.5 and preferably between 1.05 and 1.2.

The halogenation reaction according to the invention is advantageously conducted in a non-organic solvent, and more preferably in aqueous medium.

Indeed, the reaction mixture is generally composed of the reactants per se, which, generally, are employed in a more or less diluted form.

Accordingly, it is found advantageous to realize the reaction with a water/phenol of formula (III) molar ratio of less than 50, preferably less than 30 and advantageously of between 10 and 15.

The reaction is generally conducted at ambient temperature but may also be carried out within a temperature range from 0° C. to 40° C., preferably between 10° C. and 20° C.

The reaction is generally conducted under atmospheric pressure, but preferably under an inert gas atmosphere of—in particular—nitrogen.

From a practical standpoint, the halogenation is generally conducted by initially introducing the hydrohalic acid and the protected, ortho-substituted phenol.

The oxidizing agent, preferably hydrogen peroxide, is then added, preferably gradually, to the mixture.

Where appropriate, the progress of the reaction may be followed by assaying the excess halide produced.

At the end of reaction, the excess of halogen is neutralized by conventional treatment with sodium bisulphite.

The process claimed is particularly advantageous in that it avoids the use of bromine, which is a reactant which is undesirable from an industrial standpoint.

Moreover, the use of hydrobromic acid is advantageous in terms of yield as compared with the use of bromine, which involves the loss of one mole of HBr per mole of product. In the case of the present invention, the process proves to be much cleaner and hence more cost-efficient.

Although the halogenation is performed preferably by the method described above, the invention does not rule out other routes.

Accordingly, other halogenating agents, especially other brominating agents, such as bromine, N-bromo succinimide (NBS hereinafter), dibromodimethylhydantoin (DBDMH hereinafter) and N-bromophthalimide, may be used.

The reaction may be conducted in a solvent such as, for example, a halogenated or non-halogenated aliphatic hydrocarbon, preferably dichloromethane or carbon tetrachloride, a halogenated aromatic hydrocarbon such as chlorobenzene, or an aliphatic carboxylic acid having from 1 to 4 carbon atoms, preferably acetic acid.

The reaction is generally conducted at ambient temperature but may also be carried out within a temperature range from 0° C. to 100° C., preferably between 10° C. and 25° C.

The reaction is generally conducted at atmospheric pressure, but preferably under an inert gas atmosphere such as, in particular, nitrogen.

At the end of reaction, the halogenated, protected, ortho-substituted phenol is obtained, and may be employed directly in the subsequent step or else purified in accordance with conventional methods, as for example by extraction using an organic solvent such as dichloromethane, ethyl acetate or any other customary solvent.

The product is a protected phenol substituted in position 2 by an electron-donating group and halogenated in position 5, of formula (IV):

$$\underset{\underset{R_2}{\underset{|}{\phantom{X}}}}{\overset{\overset{OSO_2R_4}{\underset{|}{\phantom{X}}}}{\underset{R_3 \diagup \diagdown R}{\underset{Y \diagdown \diagup R_1}{\phantom{XXX}}}}} \qquad (IV)$$

and in said formula (IV) Y represents a halogen atom, preferably a chlorine, bromine or iodine atom, and R to $R_4$ have the meaning given above.

In accordance with the process of the invention, in a final step, the sulphonyl group is cleaved using a base so as to liberate the hydroxyl group.

According to the deprotection conditions, the invention produces a phenol which bears an electron-donating group and a halogen atom in position 5.

This operation may be conducted in aqueous medium.

For this purpose, a basic solution is employed, preferably an aqueous solution of sodium hydroxide, of potassium hydroxide or of sodium or potassium carbonate.

The concentration of the basic starting solution is not critical. The solution employed has a concentration of generally between 25% and 50% by mass.

The amount of base, expressed by the ratio between the number of moles of base and the number of moles of protected and halogenated phenol, is generally at least 1, preferably between 2 and 4.

The concentration of the halogenated, protected phenolic compound is advantageously between 2 and 5 mol/liter.

Heating takes place, generally under reflux, for a time of from 4 to 24 hours.

This operation may also be conducted in an organic solvent.

Alcohols, preferably aliphatic alcohols and more particularly methanol, ethanol and isopropanol, are solvents of choice.

The basic treatment is carried out as described above, except that, at the end of reaction, the solvent is removed by distillation.

The product obtained, which is in salt form, is then reacted with a solution of mineral acid.

The following strong acids may be employed in particular: hydrochloric acid, perchloric acid, sulphuric acid, hydrobromic acid.

The amount of acid, expressed by the ratio between the number of moles of $H^+$ ions and the number of moles of protected and halogenated phenol, is generally between 5 and 10.

The concentration of the acid solution is not critical, and it is equally possible to employ a dilute or concentrated acid solution.

Heating is carried out as before, but preferably at the reflux temperature.

A phenol is recovered which carries an electron-donating group in position 2 and a halogen atom in position 5, and which may be represented with the formula (V):

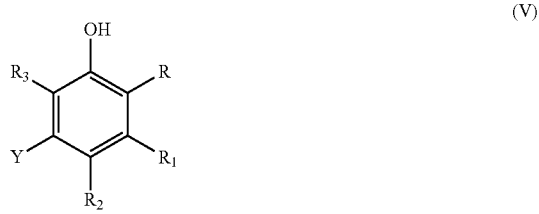

and in said formula (V) Y represents a halogen atom, preferably a chlorine, bromine or iodine atom, and R to $R_3$ have the meaning given above.

There now follow working examples of the invention, which are given for illustration and have no limitative character.

In the examples, the abbreviations have the meaning given below.

GC=guaiacol

GC-MS: guaiacol mesylate

EXAMPLES

The operating protocol is given which is reproduced in the various examples.

Mesyl chloride and zinc chloride are charged to a 250 ml (or 500 ml) reactor and then placed under an inert nitrogen atmosphere.

The mixture is heated to 120° C. and the guaiacol is then added slowly.

Following this addition, the temperature is maintained until all of the guaiacol is consumed.

The mixture is then cooled to 80° C. and the excess mesyl chloride is distilled off under reduced pressure (30 mm of mercury) at this temperature.

The crude product thus obtained is either distilled or used directly, without further purification, in the following step.

Examples 1 to 3

Protection of Guaiacol

In this series of examples, the guaiacol is protected by reaction with mesyl chloride in the presence of different Lewis acids, which are zinc salts.

Table (I) summarizes the results obtained for different zinc salts with a reaction mixture containing 12.4 g (0.1 mol) of guaiacol, 23 g (0.2 mol) of mesyl chloride and 1.5% by mass of the catalyst.

In all cases, the reaction temperature is 120° C. and the guaiacol addition time is 1 hour.

The reaction mixture is analysed by gas chromatography coupled to mass spectrometry, to determine the area percentage of guaiacol (GC) and of guaiacol mesylate (GC-MS).

TABLE (I)

| Ref. Ex. | Catalyst | GC (%) | GC-MS (%) |
|---|---|---|---|
| 1 | Zn(OAc)$_2$ | 66.06 | 32.91 |
| 2 | ZnCl$_2$ | 0.69 | 98.62 |
| 3 | Zn(OTFA)$_2$ | 60.78 | 38.76 |

It is noted that the best results are obtained using zinc chloride.

Comparative Examples 4 to 10

In this series of examples, guaiacol is protected by reaction with mesyl chloride in the presence of various Lewis acids, which are not selected according to the invention.

Table (II) summarizes the results obtained under the same conditions as before but using catalysts other than zinc catalysts, comprising the following metal cations: $Fe^{3+}$, $Ti^{4+}$, $Al^{3+}$, $Mn^{2+}$, $Cu^{2+}$, $Mo^{3+}$, $Fe^{3+}$.

TABLE (II)

| Ref. Ex. | Catalyst | GC (%) | GC-MS (%) |
|---|---|---|---|
| 4 | FeCl$_3$ | 98.36 | — |
| 5 | TiCl$_4$ | 99.05 | — |
| 6 | AlCl$_3$ | 99.01 | — |
| 7 | MnCl$_2$ | 98.72 | — |
| 8 | CuCl$_2$ | 99.09 | — |
| 9 | MoCl$_5$ | 99.00 | — |
| 10 | Fe(acac)$_3$ | 88.12 | — |

From an examination of this table it emerges that the test catalysts are not suitable for protecting the hydroxyl group, since there is no formation of guaiacol mesylate.

Examples 11 and 12

In these two examples, the amount of mesyl chloride employed is doubled relative to that of Examples 1 to 3, and different amounts of catalyst are used.

In both cases, the guaiacol is added over 4 hours.

The results obtained are set out in Table (III) below.

TABLE (III)

| Ref. Ex. | Guaiacol/MsCl molar ratio | ZnCl$_2$ (w/w %) | Time after addition (h) | GC (%) | GC-MS (%) |
|---|---|---|---|---|---|
| 11 | 10 | 5 | 0 | 43.41 | 52.91 |
|  |  |  | 1 | 31.17 | 64.72 |
|  |  |  | 2 | 25.66 | 69.74 |
| 12 | 10 | 1 | 0 | 62.54 | 28.14 |
|  |  |  | 20 | 20.44 | 74.96 |

Example 13

In this example, the reactants are introduced in a different order relative to the general protocol, since the mesyl chloride is added to the reaction mixture.

In this case, the standard operating conditions are used, except for the amount of catalyst, which is 5% by mass, and the addition time, which is 4 h.

Two hours after the end of addition of the mesyl chloride, a GC (%) of 0 and GC-MS (%) of 69.74 are obtained.

Examples 14 to 18

In this series of examples, the concentration of the zinc chloride employed is varied.

Table (IV) shows the results obtained for different amounts of zinc chloride under the standard conditions.

TABLE (IV)

| Ref. Ex. | ZnCl$_2$ (w/w %) | Time after addition (h) | GC (%) | GC-MS (%) |
|---|---|---|---|---|
| 14 | 0.5 | 4 | 63.99 | 30.73 |
| 15 | 1 | 4 | 3.82 | 94.70 |
| 16 | 1.5 | 4 | — | 93.73 |
| 17 | 2.5 | 4 | — | 94.09 |
| 18 | 5 | 4 | — | 78.05 |

Example 19

In this example, 5-bromoguaiacol is prepared in the same reactor, without separation of intermediate.

1. Protection of Guaiacol in the Form of Guaiacol Mesylate

Mesyl chloride (46 g, 0.40 mol) and zinc chloride (0.37 g) are introduced and then placed under an inert nitrogen atmosphere.

The mixture is heated to 120° C. and guaiacol (24.8 g, 0.20 mol) is then added slowly.

Following this addition, the temperature is maintained for 1 hour.

At this stage, the reaction mixture contains 98.62% of guaiacol mesylate, 0.69% of guaiacol and 0.45% of impurities (percentages calculated by area % obtained by gas chromatography coupled with mass spectrometry).

The mixture is then cooled to 80° C. and the excess mesyl chloride is distilled off under reduced pressure (30 mm of mercury) at this temperature.

Under these conditions, 19 g of mesyl chloride are recovered, with a purity of 99.95% (measured by gas chromatography coupled with mass spectrometry).

The crude product thus obtained is used directly, without further purification, in the following step.

In this example, the reaction mixture contains 96.70% of guaiacol mesylate, 0.23% of guaiacol, 0.12% of impurities and 2.75% of mesyl chloride (percentages calculated by area % obtained by gas chromatography coupled with mass spectrometry).

2. Step of Bromination of Guaiacol Mesylate

A 40% aqueous solution of hydrobromic acid (44.5 g, 0.22 mol) is added to the reaction mixture obtained in the preceding step.

The resulting mixture is stirred under an inert nitrogen atmosphere and then a 30% aqueous solution of hydrogen peroxide (25 g, 0.22 mol) is added slowly, while the temperature is held below 25° C.

Following this addition, the mixture is stirred at 10° C. for 8 h.

At this stage, the reaction mixture contains 94.3% of guaiacol 5-bromomesylate (percentage calculated by area % obtained by gas chromatography coupled with mass spectrometry).

A 20% solution of sodium hydrogen sulphite, NaHSO$_3$ (10 ml) is added and the reaction is tested with an iodine starch paper to verify that there is no longer any oxidizing agent present.

3. Deprotection of Guaiacol 5-Bromomesylate to 5-Bromoguaiacol

For the last step, a 50% aqueous solution of sodium hydroxide (50 g) is added and then the mixture is heated at reflux for 4 h or until the intermediate disappears.

The reaction mixture is then decolorized by treatment with carbon black.

The pH is then adjusted to 1 with a 35% by mass concentrated hydrochloric acid solution.

A brown solid is observed.

This solid is isolated by filtration, washed with water and then dried to give a brown solid (30.5 g, 75.1%) which has a purity of 98% (percentage calculated by area % obtained by gas chromatography coupled with mass spectrometry).

The purity of the product thus obtained can be improved by recrystallization.

For example, when 30.5 g of crude product is recrystallized from 200 ml of heptane, a white solid (18 g) is obtained with a purity of more than 98.7%.

Example 20

In this example, 5-bromoguaiacol is prepared with separation and purification of the guaiacol mesylate intermediate formed.

1. Protection of Guaiacol in the Form of Guaiacol Mesylate

Mesyl chloride (46 g, 0.40 mol) and zinc chloride (0.37 g) are introduced and then placed under an inert nitrogen atmosphere.

The mixture is heated to 120° C. and guaiacol (24.8 g, 0.20 mol) is then added slowly.

Following this addition, the temperature is maintained for 1 h.

At this stage, the reaction mixture contains 98.42% of guaiacol mesylate (percentage calculated by area % obtained by gas chromatography coupled with mass spectrometry).

The mixture is then cooled to 80° C. and the excess mesyl chloride is distilled is off under reduced pressure (50 Pa) at this temperature.

Under these conditions, 20 g of mesyl chloride are recovered, with a purity of 99.27% (percentage calculated by area % obtained by gas chromatography coupled with mass spectrometry).

The temperature is then increased to 210° C.

A fraction recovered at between 168-170° C. comprises guaiacol mesylate (28 g) with a purity of at least 98.5%.

2. Step of Bromination of Guaiacol Mesylate

A 40% aqueous solution of hydrobromic acid (31 g, 0.15 mol) is added to the guaiacol mesylate (28 g, 0.14 mol) obtained after distillation.

The resulting mixture is stirred under an inert nitrogen atmosphere and then a 30% aqueous solution of hydrogen peroxide (17 g, 0.15 mol) is added slowly, while the temperature is held below 25° C.

Following this addition, the mixture is stirred at 10° C. for 8 h.

At this stage, the reaction mixture contains 96.95% of guaiacol 5-bromomesylate (percentage calculated by area % obtained by gas chromatography coupled with mass spectrometry).

A 20% solution of sodium hydrogen sulphite, NaHSO$_3$ (10 ml) is added and the reaction is tested with an iodine starch paper to verify that there is no longer any oxidizing agent present.

3. Deprotection of Guaiacol 5-Bromomesylate to 5-Bromoguaiacol

For the last step, a 50% aqueous solution of sodium hydroxide (50 g) is added and then the mixture is heated at reflux for 4 h or until the intermediate disappears.

The reaction mixture is then decolorized by treatment with carbon black.

The pH is then adjusted to 1 with a 35% by mass concentrated hydrochloric acid solution.

A brown solid is observed.

This solid is isolated by filtration, washed with water and then dried to give a brown solid (23.5 g, 83.6%) which has a purity of 98.74% (percentage calculated by area % obtained by gas chromatography coupled with mass spectrometry).

Example 21

This example demonstrates that the zinc chloride present in the distillation bottom product from Example 20 can be recycled.

Mesyl chloride (46 g, 0.40 mol) is added to the distillation residue obtained in the distillation step of the preceding example, under an inert nitrogen atmosphere.

The mixture is heated to 120° C. and guaiacol (24.8 g, 0.20 mol) is then added slowly.

Following this addition, the temperature is maintained for 1 hour.

At this stage, the reaction mixture contains 79.31% of guaiacol mesylate, 19.33% of guaiacol and 1.12% of impurities (percentages calculated by area % obtained by gas chromatography coupled with mass spectrometry).

Example 22

In this example, guaiacol mesylate is brominated using dibromodimethylhydantoin.

Guaiacol mesylate (161.48 g, 74 mmol with a purity >98%) is mixed under an inert nitrogen atmosphere with acetic acid (800 ml) and then cooled to 15° C.

Dibromodimethylhydantoin (126.05 g, 0.44 mol) is then added in portions, during which the temperature is maintained.

The mixture is then stirred for a further 3 hours.

The reaction mixture is hydrolysed and then extracted with dichloromethane.

The organic phase is washed and, after drying over sodium sulphate and filtration, the volatiles are removed under reduced pressure (30 mm of mercury) to give a yellow solid with a quantitative yield (223 g) and a purity of greater than 99%.

The invention claimed is:

1. A process for preparing a phenol ortho-substituted by an electron-donating group and protected in the form of a sulphonic ester, the process comprising reacting a phenol ortho-substituted by an electron-donating group with a sulphonylating agent in the presence of an effective amount of a Lewis acid.

2. The process as defined in claim 1, wherein the starting ortho-substituted phenol conforms to the following formula:

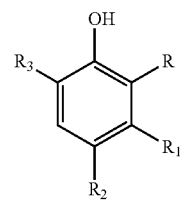

and in said formula (I):
R represents an electron-donating group, and
$R_1$, $R_2$ and $R_3$, which are identical or different, represent:
a hydrogen atom,
a linear or branched alkyl group having from 1 to 20 carbon atoms and optionally bearing one or more halogen atoms,
a cycloalkyl group having from 3 to 8 carbon atoms,
an aralkyl group having from 6 to 20 carbon atoms,
an aryl group having from 6 to 20 carbon atoms,
a halogen atom, and
an electron-donating group.

3. The process as defined in claim 1, wherein the starting ortho-substituted phenol conforms to the formula (I) in which R represents one of the following groups or functions:
a linear or a branched alkyl group having from 1 to 6 carbon atoms,
a cycloalkyl group having from 3 to 8 carbon atoms,
a phenyl group,
a benzyl or phenylethyl group,
a hydroxyl group,
a fluorine atom,
an alkoxy group having from 1 to 6 carbon atoms,
an optionally disubstituted amino group in which the identical or different substituents are linear or branched alkyl groups having from 1 to 6 carbon atoms, and
an alkylamide or an arylamide group in which the alkyl group has from 1 to 6 carbon atoms.

4. The process as defined in claim 1, wherein the starting ortho-substituted phenol is guaiacol or guaethol.

5. The process as defined in claim 1, wherein the sulphonylating agent is a compound conforming to the formula (II) below:

and in said formula (II):
R$_4$ represents a hydrocarbon group having from 1 to 20 carbon atoms, and
Z represents:
a hydroxyl group or a halogen atom, and
a group —O—SO$_2$—R$_4$' in which R$_4$', which is identical to or different from R$_4$, has the meaning given for R$_4$.

6. The process as defined in claim 5, wherein the sulphonylating agent is a compound conforming to the formula (II) in which Z represents a chlorine or bromine atom.

7. The process as defined in claim 5, wherein the sulphonylating agent is a compound conforming to the formula (II) in which R$_4$ represents:
an alkyl group having from 1 to 10 carbon atoms, which optionally bears a halogen atom, a CF$_3$ group or an ammonium group N(R$_5$)$_4$, where R$_5$, identical or different at each occurrence, represents an alkyl group having 1 to 4 carbon atoms,
a cycloalkyl group having from 3 to 8 carbon atoms,
an aryl group having from 6 to 12 carbon atoms, which optionally bears an alkyl group having from 1 to 10 carbon atoms, a halogen atom, a CF$_3$ group or an NO$_2$ group,
a group CX$_3$ in which X represents a fluorine, chlorine or bromine atom,
a CF$_2$-CF$_3$ group, and
a group C$_p$H$_a$F$_b$ in which p represents a number from 1 to 10, b represents a number from 3 to 21, and a+b=2p+1.

8. The process as defined in claim 5, wherein the sulphonylating agent is selected from the group consisting of:
triflic anhydride,
methanesulphonyl chloride,
trifluoromethanesulphonyl chloride,
benzenesulphonyl chloride, and
p-toluenesulphonyl chloride.

9. The process as defined by claim 1, wherein the Lewis acid is a compound comprising an electron-pair accepting metal or metalloid cation exhibiting borderline hardness and softness, according to an R. Pearson classification; wherein the borderline classification includes hard or soft cations with the exception of the hardest and softest cations.

10. The process as defined in claim 9, wherein the borderline cation employed has an oxidation state of at least +2.

11. The process as defined in claim 9, wherein the cation is a metal or metalloid cation of metallic or metalloid elements from group (IIb), (IVb), (Vb) or (VIb) of the Periodic Table of the Elements.

12. The process as defined in claim 9, wherein the cation is a cation selected from the group consisting of: Zn$^{2+}$, Sn$^{2+}$, Sn$^{4+}$, Sb$^{5+}$, Bi$^{3+}$, and Te$^{4+}$.

13. The process as defined in claim 9, wherein the Lewis acid is a compound comprising an anion selected from the following anions: hard anions selected from the group consisting of SO$_4^{2-}$, CH$_3$COO$^-$, C$_6$H$_5$COO$^-$, CH$_3$SO$_3^-$, CF$_3$SO$_3^-$, and CF$_3$C$_6$H$_4$SO$_3^-$, or borderline anions selected from the group consisting of Cl$^-$, Br$^-$, NO$_2^-$, and SO$_3^{2-}$.

14. The process as defined by claim 1, wherein the Lewis acid is an organic salt selected from the group consisting of acetate, propionate, benzoate, methanesulphonate and trifluoromethanesulphonate of a metallic or a metalloid element from the aforementioned groups of the Periodic Table of the Elements, and/or an inorganic salt selected from the group consisting of chloride, bromide, iodide, sulphate, oxide and analogous products of metallic or metalloid elements from the aforementioned groups of the Periodic Table of the Elements.

15. The process as defined in claim 1, wherein the Lewis acid is selected from the group consisting of antimony(V), tin(II) or (IV), zinc(II), bismuth(III) and tellurium(IV) chloride and bromide.

16. The process as defined in claim 1, wherein the active catalytic phase is deposited on an organic or inorganic support selected preferably from metal oxides, selected from the group consisting of such as aluminium oxide, silicon oxide, titanium oxide and zirconium oxide, clays.

17. A process of preparing a 5-halophenol ortho-substituted by an electron-donating group from a phenol ortho-substituted by an electron-donating group, the process comprising the following steps:
a first step of preparing a phenol ortho-substituted by an electron-donating group and protected in the form of a sulphonic ester, by the process as defined in claim 1,
a second step of halogenating a protected phenol intermediate obtained in the preceding step, in the position para to the electron-donating group, and
a third step of deprotecting the sulphonic ester function to hydroxyl.

18. The process as defined in claim 17, wherein during the second step, the halogenation reaction of the benzene ring is performed by reacting the ortho-substituted and protected phenol with a sufficient amount of a hydrohalic acid HY, where Y represents a halogen atom, in the presence of an oxidizing agent.

19. The process as defined in claim 18, wherein the halogenation reaction is performed with HY, in the presence of hydrogen peroxide.

20. The process as defined in claim 17, wherein the halogenation reaction is performed using bromine, N-bromosuccinimide or dibromodimethylhydantoin.

21. The process as defined in claim 17, wherein during the last step, the sulphonic ester function is deprotected to hydroxyl using a basic treatment.

22. The process as defined in claim 1 for preparing a 5-haloguaiacol.

23. The process as defined in claim 1, wherein the starting ortho-substituted phenol conforms to the formula (I) in which R represents one of the following groups or functions:
a linear or a branched alkyl group having from 1 to 4 carbon atoms,
a cycloalkyl group having 6 carbon atoms,
a phenyl group,
a phenylethyl group,
a hydroxyl group,
a fluorine atom,
an alkoxy group having from 1 to 4 carbon atoms in the alkyl moiety, or a phenoxy group,
an optionally disubstituted amino group in which the identical or different substituents are linear or branched alkyl groups having from 1 to 4 carbon atoms, or a phenyl group, and
an alkylamide or an arylamide group in which the alkyl group having from 1 to 4 carbon atoms, or a phenyl group.

24. The process as defined in claim 5, wherein the sulphonylating agent is a compound conforming to the formula (II) in which R$_4$ represents:
an alkyl group having from 1 to 4 carbon atoms, which optionally bears a halogen atom, a CF$_3$ group or an ammonium group N(R$_5$)$_4$, where R$_5$, identical or different at each occurrence, represents an alkyl group having from 1 to 4 carbon atoms,
a cyclohexyl group, a phenyl group which optionally bears an alkyl group having from 1 to 4 carbon atoms, optionally bearing a halogen atom, a $CF_3$ group or an $NO_2$ group, a group $CX_3$ in which X represents a fluorine, a chlorine or a bromine atom, a $CF_2$-$CF_3$ group, and a group $C_p H_a F_b$ in which p represents a number from 1 to 10, b represents a number from 3 to 21, and a+b=2p+1.

25. The process as defined in claim 7, wherein when the phenyl group bears an alkyl group, the alkyl group comprises from 1 to 10 carbon atoms.

26. The process as defined in claim 25, wherein the alkyl group is a methyl or ethyl group.

27. The process as defined in claim 9, wherein the borderline cation employed has an oxidation state of +3, +4 or +5.

28. The process as defined in claim 9, wherein the cation is $Zn^{2+}$.

29. The process as defined in claim 9, wherein the Lewis acid is a compound comprising an anion of $Cl^-$ or $Br^-$.

30. The process as defined in claim 1, wherein the Lewis acid comprises zinc chloride.

31. The process as defined in claim 18, wherein the halogenation reaction is performed with HBr, in the presence of hydrogen peroxide.

32. The process as defined in claim 1 for preparing a 5-bromoguaiacol.

* * * * *